US012741990B2

(12) United States Patent
Rajyaguru et al.

(10) Patent No.: US 12,741,990 B2
(45) Date of Patent: Sep. 22, 2026

(54) PEPTIDE FOR DISASSEMBLY OF PROTEIN AGGREGATES AND METHODS THEREOF

(71) Applicant: INDIAN INSTITUTE OF SCIENCE, Kamataka (IN)

(72) Inventors: Purusharth I Rajyaguru, Kamataka (IN); Mani Garg, Kamataka (IN); Nayana V, Kamataka (IN)

(73) Assignee: INDIAN INSTITUTE OF SCIENCE, Kamataka (IN)

( * ) Notice: Subject to any disclaimer, the term of this patent is extended or adjusted under 35 U.S.C. 154(b) by 0 days.

(21) Appl. No.: 19/292,131

(22) Filed: Aug. 6, 2025

(65) Prior Publication Data

US 2026/0167672 A1 Jun. 18, 2026

(51) Int. Cl.

*C07K 14/00* (2006.01)
*A61K 38/00* (2006.01)
*C07K 7/08* (2006.01)

(52) U.S. Cl.

CPC .............. *C07K 14/001* (2013.01); *C07K 7/08* (2013.01); *A61K 38/00* (2013.01)

(58) Field of Classification Search

None

See application file for complete search history.

(56) References Cited

PUBLICATIONS

Madine et al., Evaluation of b-Alanine- and GABA-Substituted Peptides as Inhibitors of Disease-Linked Protein Aggregation. ChemBioChem 10:1982-1987, 2009.*

Bett et al., Structure-Activity Relationships in Peptide Modulators of β-Amyloid Protein Aggregation: Variation in α,α-Disubstitution Results in Altered Aggregate Size and Morphology. Neurosci. 1 (9): 608-626, 2010.*

* cited by examiner

*Primary Examiner* — Ruixiang Li

(74) *Attorney, Agent, or Firm* — Ohlandt, Greeley and Perle, L.L.P.

(57) ABSTRACT

The present disclosure provides a novel, potent and effective disassembly biomolecule, specifically a peptide, and a robust method or a platform technology for synthesizing and/or identifying disassembly biomolecules that are capable of inducing disassembly of protein aggregates associated with neurodegenerative diseases.

4 Claims, 4 Drawing Sheets

Figure 1:
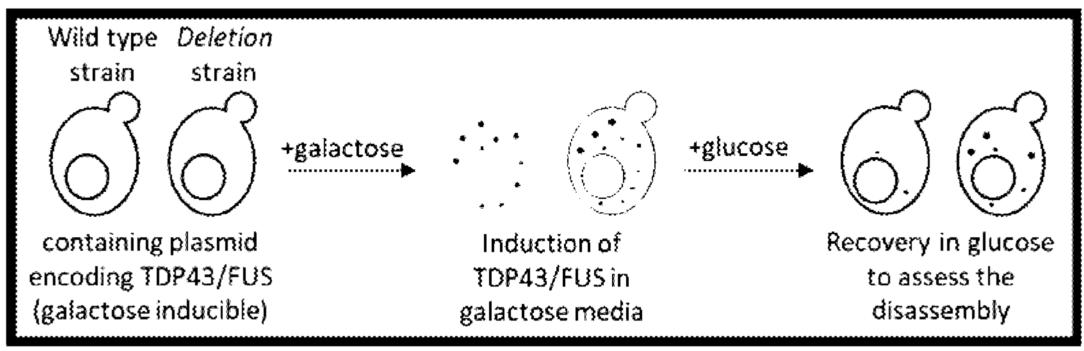

Specification includes a Sequence Listing.

SEQUENCE LISTING

```
Sequence total quantity: 7
SEQ ID NO: 1            moltype = AA  length = 27
FEATURE                 Location/Qualifiers
source                  1..27
                        mol_type = protein
                        organism = synthetic construct
SEQUENCE: 1
FGGFRGRGGF GGFRGRGGFG GFRGRGG                                       27

SEQ ID NO: 2            moltype = AA  length = 18
FEATURE                 Location/Qualifiers
source                  1..18
                        mol_type = protein
                        organism = synthetic construct
SEQUENCE: 2
FGGFRGRGGF GGFRGRGG                                                 18

SEQ ID NO: 3            moltype = AA  length = 36
FEATURE                 Location/Qualifiers
source                  1..36
                        mol_type = protein
                        organism = synthetic construct
SEQUENCE: 3
FGGFRGRGGF GGFRGRGGFG GFRGRGGFGG FRGRGG                             36

SEQ ID NO: 4            moltype = AA  length = 45
FEATURE                 Location/Qualifiers
source                  1..45
                        mol_type = protein
                        organism = synthetic construct
SEQUENCE: 4
FGGFRGRGGF GGFRGRGGFG GFRGRGGFGG FRGRGGFGGF RGRGG                   45

SEQ ID NO: 5            moltype = AA  length = 54
FEATURE                 Location/Qualifiers
source                  1..54
                        mol_type = protein
                        organism = synthetic construct
SEQUENCE: 5
FGGFRGRGGF GGFRGRGGFG GFRGRGGFGG FRGRGGFGGF RGRGGFGGFR GRGG         54

SEQ ID NO: 6            moltype = AA  length = 63
FEATURE                 Location/Qualifiers
source                  1..63
                        mol_type = protein
                        organism = synthetic construct
SEQUENCE: 6
FGGFRGRGGF GGFRGRGGFG GFRGRGGFGG FRGRGGFGGF RGRGGFGGFR GRGGFGGFRG  60
RGG                                                                 63

SEQ ID NO: 7            moltype = AA  length = 72
FEATURE                 Location/Qualifiers
source                  1..72
                        mol_type = protein
                        organism = synthetic construct
SEQUENCE: 7
FGGFRGRGGF GGFRGRGGFG GFRGRGGFGG FRGRGGFGGF RGRGGFGGFR GRGGFGGFRG  60
RGGFGGFRGR GG                                                       72
```

PEPTIDE FOR DISASSEMBLY OF PROTEIN AGGREGATES AND METHODS THEREOF

SEQUENCE LISTING XML

Sequence Listing XML file with the name IP81652-IISC.xml, created on Aug. 20, 2025, and having a file size of 7,000 bytes is incorporated herein by reference in its entirety.

TECHNICAL FIELD

The present invention in general relates to the field of genetic and protein engineering, and pharmacology. Particularly, the present disclosure relates to a peptide which is a disassembly biomolecule capable of disassembling protein aggregates, along with a method for synthesizing and/or identifying disassembly biomolecules. These biomolecules are capable of targeting and disassembling protein aggregates associated with various disorders, offering potential therapeutic applications.

BACKGROUND OF THE DISCLOSURE

Several studies have been conducted to show the presence of toxic protein aggregates in the cells and their role in contributing to the pathology of several disorders. One of the neurological disorders discussed with respect to the present disclosure is Amyotrophic lateral sclerosis (ALS). ALS, also known as Lou Gehrig's disease, is a progressive, fatal, neurodegenerative disorder that affects the nerve cells in the brain and the spinal cord. 5-10% of ALS cases are familial. Genes encoding FET [Fused in Sarcoma (FUS), Ewing Sarcoma breakpoint Region 1 (EWSR1) and TATA-box binding protein-Associated Factor 15 (TAF15)] and Tar DNA binding protein (TDP)-43 proteins have emerged as the most studied class of genes in the context of ALS. Several mutations in these genes have been identified in ALS patients. The above proteins are predominantly nuclear-localized; however, in ALS patients, they are often found in cytoplasmic aggregates, which resemble RNA-protein complexes referred to in general as RNP condensates. Several defects have been reported in patients due to this mis-localization. Some of them are attributed to the loss of their nuclear function (such as transcription and splicing), whereas others are due to the gain of aberrant cytoplasmic function (mRNA translation/stability). Aberrant cytoplasmic phase transitions are instrumental in the manifestation of several defects observed in ALS/FTD patients. Aggregates of FUS and TDP43 proteins in patient samples harbour RNA granule components, leading to the idea that these aggregates are aberrant forms of RNA granules. Such observations have also been reported for other nuclear RNA-binding proteins such as hnRNPAT and hnRNPA2. Identification of molecules that can disrupt/dissolve these aggregates is an effective therapeutic option against these neurodegenerative diseases. Research focused on finding such molecules has received attention in recent times. Few studies focused on anti-aggregation and/or pro-disaggregation therapeutic properties of peptides have been reported for ALS. Several mutants of FUS and TDP-43 have been studied for their role in ALS. FUS P525L is a well-characterized mutant that has been associated with a severe juvenile form of ALS. A315T and M337V are two well-characterized mutants of TDP-43. Upon stress, these mutants localize to stress granules and the granules persist even 24 h after removal of stress. Stress granules (SGs) are dynamic RNA-protein complexes in the cytoplasm that are sites of mRNA storage. SGs assemble upon stress through the process of liquid-liquid phase separation and disassemble once cells return to normal conditions. Purified A315T and M337V accelerate aggregation. These mutants have helped us understand the disease progression and pathology.

A critical barrier in ALS therapy is the dissolution of toxic cytoplasmic aggregates of FUS and TDP-43, two proteins implicated in ALS. FUS is a DNA/RNA-binding protein implicated in various cellular processes such as transcription, splicing and mRNA export. It was originally identified as an oncogene in human myxoid liposarcomas. Many patient mutations lead to cytoplasmic accumulation of the predominantly nuclear FUS in the cytoplasm. This is similar to observations made with TDP43, another gene implicated in ALS. The disease phenotypes in ALS could be due to loss of nuclear function, gain of toxic cytoplasmic role or both. Mice expressing FUS lacking NLS sequence show cytoplasmic FUS localization and motor neuron apoptosis, which is not observed in FUS knockout mice, suggesting that a toxic gain of cytoplasmic function is responsible for ALS pathology. Significant progress has been made towards understanding the role of FUS phase separation in vitro. Recently an ultrasensitive single droplet surface-enhanced Raman spectroscopy (SERS) technique has been developed and used to study the FUS condensates and understand its phase behaviour. Using single molecular FRET, two coexisting distinct confirmational monomeric subpopulations have been identified.

Identification of molecules that can disrupt or dissolve these aggregates is an effective therapeutic option against neurodegenerative diseases and also remains a significant challenge. Research focused on finding such molecules has received increasing attention in recent years. The idea that aberrant RNA granules contribute to ALS pathogenesis has led to tremendous interest in identifying small molecules capable of overcoming the disassembly-resistant nature of these condensates. A very recent and emerging field of condensate-modifying drugs (C-mods) has garnered substantial interest—these drugs have been broadly classified into several categories, including: 1) Dissolvers, 2) Inducers, 3) Localizers, and 4) Morphers. However, despite this growing interest, there are currently no effective drugs available that can reliably dissolve such toxic protein aggregates.

Thus, there exists a critical need for the development of novel therapeutic agents and a robust method or platform for synthesizing and/or identifying novel biomolecules/agents for the treatment of neurological disorders.

SUMMARY OF THE DISCLOSURE

The present disclosure relates to a peptide that functions as a disassembly biomolecule. Particularly, the present disclosure provides a peptide that is capable of inducing the disassembly of protein aggregates associated with neurodegenerative diseases. More particularly, the present disclosure provides a peptide comprising an amino acid sequence set forth as $(FGGFRGRGG)_n$ or a sequence having at least 90% sequence identity to said amino acid sequence, wherein 'n' is an integer from 2 to 8, and wherein said peptide is capable of inducing disassembly of protein aggregates.

In some embodiments, the peptide comprises repeat units (n=3) of the amino acid motif $(FGGFRGRGG)_3$, i.e., an amino acid sequence set forth as FGGFRGRGGFGGFRGRGGFGGFRGRGG (SEQ ID No. 1) or a sequence having at least 90% sequence identity to said amino acid sequence.

In some embodiments, the peptide is derived from a protein selected from a group comprising Sbp1, Psp2, Gbp2, Scd6, Npl3, Gar1, Ncl1, Nsr1, Nop1/3, Dbp1/2, Ski2, or Lge1.

In some embodiments, protein aggregates are selected from a group comprising TDP43 protein aggregates, FUS protein aggregates, Tau protein aggregates, alpha-synuclein protein aggregates, EWSR1 protein aggregates, TAF15 protein aggregates or combinations thereof.

In some embodiments, the peptide is a synthetic peptide comprising an amino acid sequence as set forth as SEQ ID NO. 1, SEQ ID NO. 2, SEQ ID NO. 3, SEQ ID NO. 4, SEQ ID NO. 5, SEQ ID NO. 6, or SEQ ID NO. 7, wherein said peptide is capable of inducing disassembly of TDP43 protein aggregates, FUS protein aggregates, or both.

The present disclosure also provides a composition comprising the peptide of the present disclosure (as described above) and a pharmaceutically acceptable excipient.

The present disclosure also relates to a method to synthesize a disassembly biomolecule that is capable of disassembling protein aggregates. Particularly, the present disclosure provides a method to synthesize a disassembly biomolecule that is capable of disassembling protein aggregates, said method comprising:

a) identifying a disassembly factor in a model system; and
b) designing and synthesizing the disassembly biomolecule based on said disassembly factor, wherein the disassembly biomolecule is capable of disassembling protein aggregates.

In some embodiments, the step a) of identifying the disassembly factor in a model system comprises:

i) providing a model system capable of expressing a protein and formation of protein aggregates, under a galactose-inducible promoter;
   wherein the model system is a host cell which is a wild-type host cell and a mutant host cell deficient in a candidate disassembly factor;
ii) culturing the wild-type host cell and the mutant host cell in a galactose-containing medium to induce expression of said protein and formation of the protein aggregates;
iii) culturing the wild-type host cell and the mutant host cell in a glucose-containing medium to inhibit expression of said protein and formation of the protein aggregates;
iv) comparing the amount of the protein in the protein aggregates between the wild-type host cell and the mutant host cell; and
v) identifying the candidate disassembly factor to be the disassembly factor if the mutant host cell has more protein in the protein aggregates compared to the wild-type host cell.

In some embodiments, the host cell is a yeast cell.

In some embodiments, the yeast cell is selected from *Saccharomyces cerevisiae, Pichia pastoris*, or *Schizosaccharomyces pombe.*

In some embodiments, the disassembly factor is a protein containing low-complexity sequences and/or RGG/RG repeat motifs.

In some embodiments, the disassembly factor is a protein or a derivative thereof, selected from a group comprising Sbp1, Psp2, Gbp2, Scd6, Npl3, Gar1, Ncl1, Nsr1, Nop1/3, Dbp1/2, Ski2, and Lge1.

In some embodiments, the method further comprises a step of assessing the ability of the disassembly biomolecule to disassemble the protein aggregates in an in vitro assay or an in-cell sedimentation assay.

The present disclosure also provides a method to disassemble protein aggregates. More particularly, the present disclosure provides a method to disassemble protein aggregates comprising contacting the peptide (as described above), or the composition (as described above), with target cell(s) comprising said protein aggregates, to disassemble the protein aggregates.

In some embodiments, the target cells are selected from a group comprising mammalian cells, neuroblastoma cells, motor neurons, cortical neurons, astrocytes, oligodendrocytes, primary neuronal cultures, microglia, induced pluripotent stem cells (iPSCs), HEK293 cells, HeLa cells, or other relevant cell lines.

The present disclosure also provides the use of the peptide (as described above) and the composition (as described above). More particularly, the present disclosure provides a peptide comprising an amino acid sequence set forth as $(FGGFRGRGG)_n$ or a sequence having at least 90% sequence identity to said amino acid sequence, wherein 'n' is an integer from 2 to 8, for use as a medicament.

In some embodiments, the present disclosure provides a peptide having sequence selected from SEQ ID NO. 1 to 7 for use as a medicament. The present disclosure provides a composition comprising a peptide having a sequence selected from SEQ ID NO: 1 to 7 for use as a medicament.

BRIEF DESCRIPTION OF THE ACCOMPANYING FIGURES

In order that the present disclosure may be readily understood and put into practical effect, reference will now be made to exemplary embodiments as illustrated with reference to the accompanying figures. The figures together with detailed description below, are incorporated in and form part of the specification, and serve to further illustrate the embodiments and explain various principles and advantages, where:

FIG. 1 represents the step a) of the claimed method for identifying a disassembly factor, where positive targets affecting the disassembly of TDP43/FUS were identified using a yeast model system.

Figure 2:
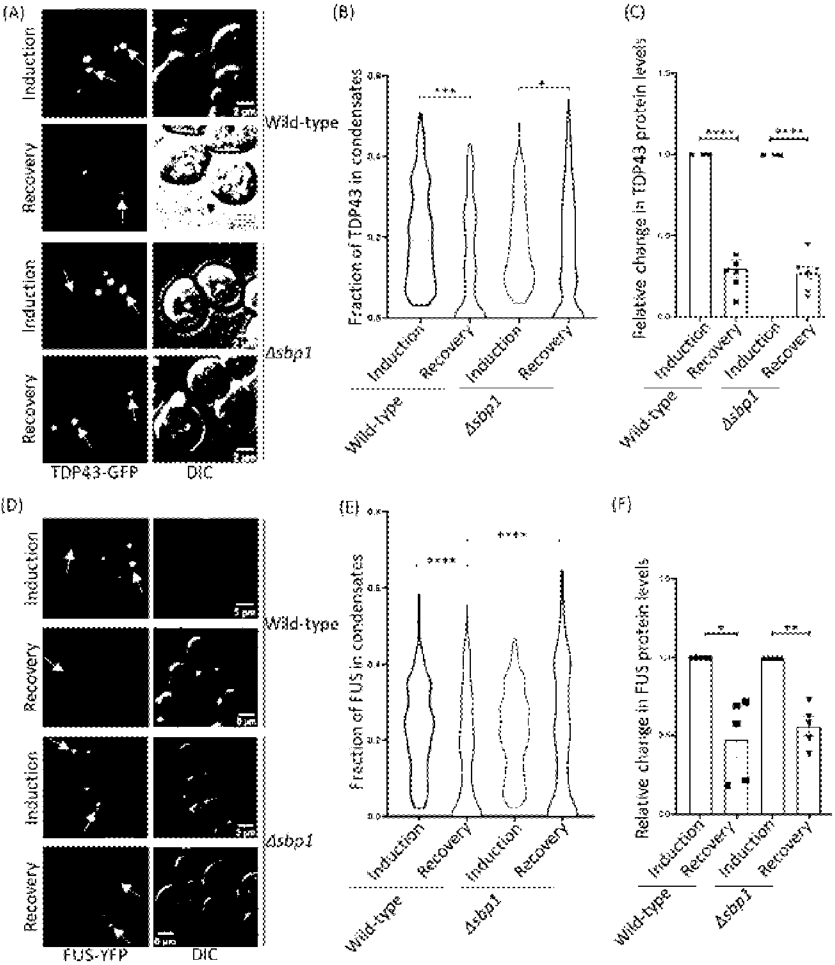

FIG. 2 shows the results of step a) of the claimed method demonstrating that Δsbp1 yeast cells are defective in the disassembly of TDP43 and FUS condensates in yeast cells. FIG. 2 (A): Representative images for the microscopy analysis of wild-type and Δsbp1 cells transformed with the Gal-TDP43-GFP plasmid [Scale bar=2 um]. FIG. 2 (B): Graph representing the fraction of the TDP43 protein present in condensates per cell. FIG. 2 (C): Graph depicting the relative change in TDP43 protein levels as compared to the respective induction condition. FIG. 2 (D): Representative images for the microscopy analysis of wild-type and Δsbp1 cells transformed with Gal-FUS-YFP plasmid [Scale bar=5 um]. FIG. 2 (F): Graph depicting the relative change in FUS protein levels compared to the respective induction condition.

Error bars in all graphs represent mean±SEM, and the same color points depict the data from a single experimental set for all the graphs. *, , *, and **** denote p-value<0.05, <0.01, <0.001, and <0.0001, respectively.

Figure 3:
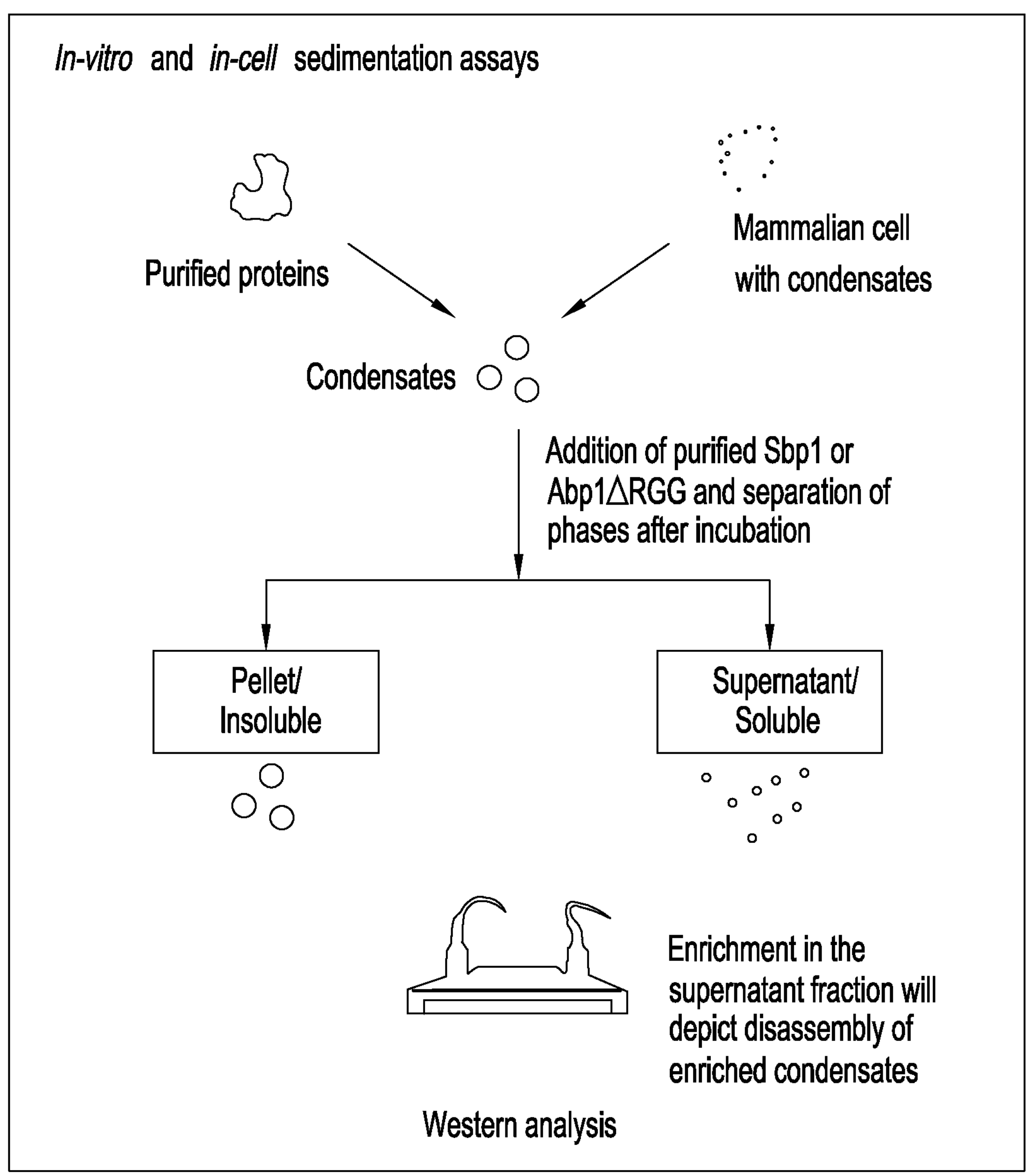

FIG. 3 is a schematic representation of the in-vitro and in-cell sedimentation assays used to assess the ability of the disassembly biomolecule of the present disclosure to disassemble protein aggregates.

Figure 4:
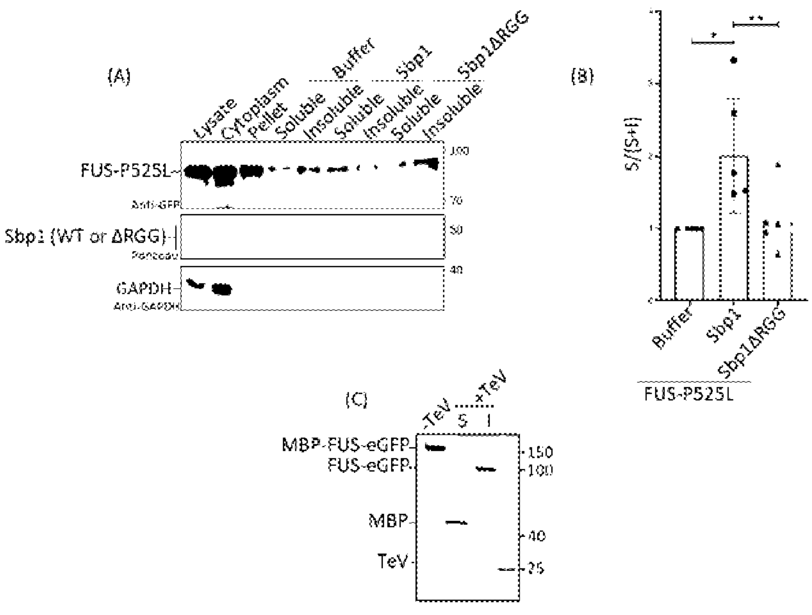
Figure 4:
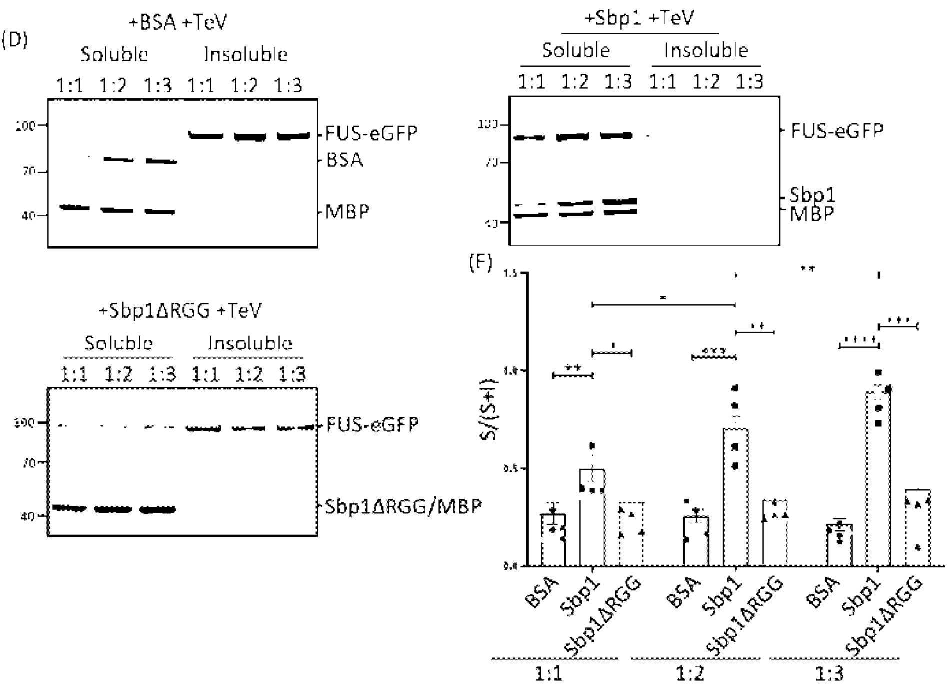

FIG. 4 shows the results demonstrating that Sbp1, but not Sbp1ΔRGG, disassembles FUS condensates. FIG. 4 (A): Western analysis of the different fractions from FUS-P525L in-cell sedimentation assay. The different fraction loadings are as follows: lysate: 7.5%, cytoplasm: 7.5%, pellet: 15%, soluble: 60%, and insoluble: 60%. GAPDH serves as the control for the assay, and ponceau reflects the purified protein added to the respective reaction. Values on the right represent the position of different molecular weight ladder bands in kDa. FIG. 4 (B): Quantitation of the amount of protein in the soluble fraction from experiments as done in A. The band intensities were calculated using ImageJ, and the fraction of protein in the soluble phase was calculated by S/(S+I), where S and I represent the protein in the soluble and the insoluble fractions, respectively. Significance was calculated by using student-paired t-test analysis (n=6). FIG. 4 (C) Coomassie-stained protein gels depicting the partitioning of FUS to the insoluble (I) phase after the cleavage of MBP-tag using TeV protease. S denotes the soluble phase. Values on the right represent the position of different molecular weight ladder bands in kDa. FIG. 4 (D) Coomassie-stained protein gels depicting the fractionation of FUS to soluble and insoluble phases in the presence of buffer, BSA, Sbp1, Sbp1ΔRGG. The ratio reflects the amount of FUS: test protein taken for the assay. Sbp1ΔRGG and MBP migrate at the same position and hence appear as a single band. Values on the left represent the position of different molecular weight ladder bands in kDa. FIG. 4 (E) Quantitation of the fraction of FUS protein present in the soluble phase from 7 independent experiments (n=7) as performed in D. Significance was calculated by a student-paired t-test analysis. Error bars represent mean±SEM, and the same color points depict the data from a single experimental set. *, , * and **** denote p-value≤0.05, ≤0.01, ≤0.001, and ≤0.0001, respectively.

Figure 5:
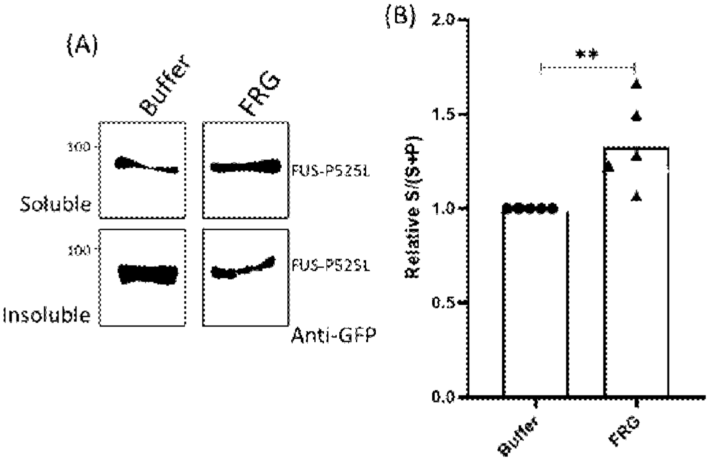

FIG. 5 shows the results of testing of the FRG peptide for disassembling FUS-P525L condensates. FIG. 5 (A): Western analysis of the soluble and insoluble fractions from FUS-P525L in-cell sedimentation assay after the addition of buffer or FRG peptide. Values on the left represent the position of different molecular weight ladder bands in kDa. FIG. 5 (B) Quantitation of the amount of protein in the soluble fraction from experiments as done in A. The band intensities were calculated using ImageJ, and the fraction of protein in the soluble phase was calculated by S/(S+I), where S and I represent the protein in the soluble and the insoluble fractions, respectively. Significance was calculated by using student-paired t-test analysis (n=6). Significance was calculated by a student-paired t-test analysis. Error bars represent mean±SEM, and the same color points depict the data from a single experimental set. ** denotes p-value≤0.01.

BRIEF DESCRIPTION OF SEQUENCES OF THE PRESENT DISCLOSURE

SEQ ID NO. 1 represents the amino acid sequence of the FRG peptide of the present disclosure where n=3:

FGGFRGRGGFGGFRGRGGFGGFRGRGG

SEQ ID NO. 2 represents the amino acid sequence of the peptide of the present disclosure where n=2:

FGGFRGRGGFGGFRGRGG

SEQ ID NO. 3 represents the amino acid sequence of the peptide of the present disclosure where n=4:

FGGFRGRGGFGGFRGRGGFGGFRGRGGFGGFRGRGG

SEQ ID NO. 4 represents the amino acid sequence of the peptide of the present disclosure where n=5:

FGGFRGRGGFGGFRGRGGFGGFRGRGGFGGFRGRGGFGGFRGRGG

SEQ ID NO. 5 represents the amino acid sequence of the peptide of the present disclosure where n=6:

FGGFRGRGGFGGFRGRGGFGGFRGRGGFGGFRGRGGFGGFRGRGGFGGF
RGRGG

SEQ ID NO. 6 represents the amino acid sequence of the peptide of the present disclosure where n=7:

FGGFRGRGGFGGFRGRGGFGGFRGRGGFGGFRGRGGFGGFRGRGGFGGF
RGRGGFGGFRGRGG

SEQ ID NO. 7 represents the amino acid sequence of the peptide of the present disclosure where n=8:

FGGFRGRGGFGGFRGRGGFGGFRGRGGFGGFRGRGGFGGFRGRGGFGGF
RGRGGFGGFRGRGGFGGFRGRGG

DESCRIPTION OF THE DISCLOSURE

Unless otherwise defined, all terms used in the disclosure, including technical and scientific terms, have meaning as commonly understood by one of ordinary skill in the art to which this invention belongs. By means of further guidance, term definitions are included for better understanding of the present disclosure.

As used herein, the singular forms 'a', 'an' and 'the' include both singular and plural referents unless the context clearly dictates otherwise.

The term 'comprising', 'comprises' or 'comprised of' as used herein are synonymous with 'including', 'includes', 'containing' or 'contains' and are inclusive or open-ended and do not exclude additional, non-recited members, elements, or method steps.

The recitation of numerical ranges by endpoints includes all numbers and fractions subsumed within the respective ranges, as well as the recited endpoints.

The term 'about' as used herein when referring to a measurable value such as a parameter, an amount, a temporal duration, and the like, is meant to encompass variations of 10% or less, preferably ±5% or less, more preferably 10% or less and still more preferably +0.1% or less of and from the specified value, insofar such variations are appropriate to perform the present disclosure. It is to be understood that the value to which the modifier 'about' refers is itself also specifically and preferably disclosed.

The term "induces" is intended to cover non-exclusive inclusion such as "promotes", "helps" or "aids".

The term "delivering" is intended to cover "administering", "incubating", "contacting", and "treating".

As used herein, the term/phrase 'neurological disorders' is used interchangeably with 'neurodegenerative disease' and in the context of the present invention refers to a class of diseases in which specific proteins misfold, aggregate, and accumulate abnormally within neurons or glial cells. These protein aggregates disrupt cellular function and ultimately lead to neurodegeneration. These are, but not limited to, Amyotrophic Lateral Sclerosis (ALS), Frontotemporal Dementia (FTD), Alzheimer's Disease (AD), Multiple System Atrophy (MSA), and Parkinson's Disease (PD).

As used herein, the term 'in vitro' refers to procedures/methods conducted externally in an artificial environment or laboratory/industrial setting, i.e. outside of a living organism.

As used herein, the term 'in-cell' indicates that an assay/method is performed using, cultured cells (e.g., yeast, mammalian cells), and the protein of interest is expressed within the cellular environment.

As used herein, the phrase 'disassembling protein aggregates' refers to a process by which pre-formed or misfolded protein aggregates—such as amyloid fibrils, stress granules, or pathological condensates often associated with neurological diseases/disorders—are modulated, dissolved, or broken apart/down into smaller, soluble and non-toxic forms through the action of biomolecules or therapeutic agents.

As used herein, the term 'peptide' refers to a short polymer composed of amino acids linked together by peptide bonds, typically containing 2 to about 50 amino acids, and exists in several forms such as dipeptides, tripeptides, oligopeptides, polypeptides, or cyclic peptides.

Neurodegenerative diseases such as Amyotrophic lateral sclerosis (ALS) are fatal in nature and marked by degeneration of upper and lower motor neurons. Mutations in many proteins, including TDP43 and FUS, have been identified and correlated with the disease phenotype.

One of the characteristic features of these proteins in ALS is their mis localisation to the cytoplasm and the formation of cytoplasmic RNP condensates. The sequestration of TDP43 and FUS to these structures results in their 'loss of normal nuclear function' and, at the same time, 'gain of new cytoplasmic function', thus leading to the diseasephenotype.

Thus, one of the main objectives of the present disclosure is to develop a disassembly biomolecule capable of inducing break down or disassembling protein aggregates or toxic cytoplasmic RNP condensates associated with neurodegenerative diseases, and wherein such disassembly biomolecule has therapeutic application.

Yet another objective of the present disclosure is to develop a robust method or a platform technology for identifying and/or synthesizing novel disassembly biomolecules capable of disassembling protein aggregates or pathological condensates associated with neurodegenerative diseases.

Still another objective of the present disclosure is to understand the role of low-complexity peptide sequences in disassembly of FUS and TDP-43 aggregates implicated in ALS pathology.

To achieve the aforesaid objectives, the present disclosure provides a novel, potent and effective disassembly biomolecule, specifically a peptide; and a robust method or a platform technology for synthesizing and/or identifying disassembly biomolecules that are capable of inducing disassembly of protein aggregates associated with neurodegenerative diseases.

Peptide

The present disclosure pertains to a peptide that functions as a disassembly biomolecule. Particularly, the present disclosure provides a peptide that is capable of inducing the disassembly of protein aggregates associated with neurodegenerative diseases. The present disclosure provides a synthetic peptide with low complexity sequence or repetitive motifs, such as RGG/RG motifs. Particularly, the peptide is rich in phenylalanine (F), arginine (R), and glycine (G) amino acids.

More particularly, the present disclosure provides a peptide comprising an amino acid sequence set forth as $(FGGFRGRGG)_n$ or a sequence having at least 90% sequence identity to said amino acid sequence, wherein 'n' is an integer from 2 to 8, and wherein said peptide is capable of inducing disassembly of protein aggregates.

In some embodiments, the peptide comprises repeat units of the amino acid motif $(FGGFRGRGG)_n$, or a sequence having at least 90% sequence identity to said amino acid sequence, wherein n is an integer from 2 to 8.

In some embodiments, the peptide comprises amino acid sequence set forth as $(FGGFRGRGG)_{2-8}$, or a sequence having at least 91%, 92%, 93%, 94%, 95%, 96%, 97%, 98%, or 99% sequence identity to said amino acid sequence.

In some embodiments, n refers to the repeat units of the amino acid motif $(FGGFRGRGG)_n$ and is 2, 3, 4, 5, 6, 7, or 8.

In some embodiments, the peptide comprises repeat units (n=3) of the amino acid motif $(FGGFRGRGG)_3$, i.e., an amino acid sequence set forth as FGGFRGRGGFGGFRGRGGFGGFRGRGG (SEQ ID No. 1) or a sequence having at least 90% sequence identity to said amino acid sequence.

In some embodiments, the peptide comprises repeat units (n=3) of the amino acid motif $(FGGFRGRGG)_3$, i.e., an amino acid sequence set forth as FGGFRGRGGFGGFRGRGGFGGFRGRGG (SEQ ID No. 1).

In some embodiments, the peptide comprises repeat units (n=2) of the amino acid motif $(FGGFRGRGG)_2$, i.e., an amino acid sequence set forth as FGGFRGRGGFGGFRGRGG (SEQ ID NO. 2), or a sequence having at least 90% sequence identity to said amino acid sequence.

In some embodiments, the peptide comprises repeat units (n=2) of the amino acid motif $(FGGFRGRGG)_2$, i.e., an amino acid sequence set forth as FGGFRGRGGFGGFRGRGG (SEQ ID NO. 2).

In some embodiments, the peptide comprises repeat units (n=4) of the amino acid motif $(FGGFRGRGG)_4$, i.e., an amino acid sequence set forth as FGGFRGRGGFGGFRGRGGFGGFRGRGGFGGFRGRGG (SEQ ID NO. 3), or a sequence having at least 90% sequence identity to said amino acid sequence.

In some embodiments, the peptide comprises repeat units (n=4) of the amino acid motif $(FGGFRGRGG)_4$, i.e., an amino acid sequence set forth as FGGFRGRGGFGGFRGRGGFGGFRGRGGFGGFRGRGG (SEQ ID NO. 3).

In some embodiments, the peptide comprises repeat units (n=5) of the amino acid motif $(FGGFRGRGG)_5$, i.e., an amino acid sequence set forth as FGGFRGRGGFGGFRGRGGFGGFRGRGGFGGFRGRGGFGGFRGRGG (SEQ ID NO. 4), or a sequence having at least 90% sequence identity to said amino acid sequence.

In some embodiments, the peptide comprises repeat units (n=5) of the amino acid motif $(FGGFRGRGG)_5$, i.e., an amino acid sequence set forth as FGGFRGRGGFGGFRGRGGFGGFRGRGGFGGFRGRGGFGGFRGRGG (SEQ ID NO. 4).

In some embodiments, the peptide comprises repeat units (n=6) of the amino acid motif $(FGGFRGRGG)_6$, i.e., an amino acid sequence set forth as FGGFRGRGGFGGFRGRGGFGGFRGRGGFGGFRGRGGFGGFRGRGGFGGFRGRGG (SEQ ID NO. 5), or a sequence having at least 90% sequence identity to said amino acid sequence.

In some embodiments, the peptide comprises repeat units (n=6) of the amino acid motif $(FGGFRGRGG)_6$, i.e., an amino acid sequence set forth as FGGFRGRGGFGGFRGRGGFGGFRGRGGFGGFRGRGGFGGFRGRGGFGGFRGRGG (SEQ ID NO. 5).

In some embodiments, the peptide comprises repeat units (n=7) of the amino acid motif $(FGGFRGRGG)_7$, i.e., an amino acid sequence set forth as FGGFRGRGGFGGFRGRGGFGGFRGRGGFGGFRGRGGFGGFRGRGGFGGFRGRGGF GGFRGRGG (SEQ ID NO. 6), or a sequence having at least 90% sequence identity to said amino acid sequence.

In some embodiments, the peptide comprises repeat units (n=7) of the amino acid motif $(FGGFRGRGG)_7$, i.e., an amino acid sequence set forth as FGGFRGRGGFGGFRGRGGFGGFRGRGGFGGFRGRGGFGGFRGRGGFGGFRGRGGF GGFRGRGG (SEQ ID NO. 6).

In some embodiments, the peptide comprises repeat units (n=8) of the amino acid motif $(FGGFRGRGG)_8$, i.e., an amino acid sequence set forth as FGGFRGRGGFGGFRGRGGFGGFRGRGGFGGFRGRGGFGGFRGRGGFGGFRGRGGF GGFRGRGGFGGFRGRGG (SEQ ID NO. 7).

In some embodiments, the peptide comprises repeat units (n=8) of the amino acid motif $(FGGFRGRGG)_8$, i.e., an amino acid sequence set forth as FGGFRGRGGFGGFRGRGGFGGFRGRGGFGGFRGRGGFGGFRGRGGFGGFRGRGGF GGFRGRGGFGGFRGRGG (SEQ ID NO. 7), or a sequence having at least 90% sequence identity to said amino acid sequence.

In some embodiments, the peptide is (SEQ ID NO. 1)
FGGFRGRGGFGGFRGRGGFGGFRGRGG, (SEQ ID NO. 2)
FGGFRGRGGFGGFRGRGG, (SEQ ID NO. 3)
FGGFRGRGGFGGFRGRGGFGGFRGRGGFGGFRGRGG,
or (SEQ ID NO. 4)
FGGFRGRGGFGGFRGRGGFGGFRGRGGFGGFRGRGGFGGFRGRGG;
or a sequence having at least 90% sequence identity to sequence as set forth in any one of SEQ ID NO. 1 to 7.

In some embodiments, the peptide is (SEQ ID NO. 1)
FGGFRGRGGFGGFRGRGGFGGFRGRGG, (SEQ ID NO. 2)
FGGFRGRGGFGGFRGRGG, (SEQ ID NO. 3)
FGGFRGRGGFGGFRGRGGFGGFRGRGGFGGFRGRGG,
or (SEQ ID NO. 4)
FGGFRGRGGFGGFRGRGGFGGFRGRGGFGGFRGRGGFGGFRGRGG;

(SEQ ID NO. 5)
FGGFRGRGGFGGFRGRGGFGGFRGRGGFGGFRGRGGFGGFRGRGGFGGFR

GRGG

-continued (SEQ ID NO. 6)
FGGFRGRGGFGGFRGRGGFGGFRGRGGFGGFRGRGGFGGFRGRGGFGGFR

GRGGFGGFRGRGG,
or (SEQ ID NO. 7)
FGGFRGRGGFGGFRGRGGFGGFRGRGGFGGFRGRGGFGGFRGRGGFGGFR

GRGGFGGFRGRGGFGGFRGRGG,
or a sequence having at least 90% sequence identity to sequence as set forth in any one of SEQ ID NO. 1 to 7.

In some embodiments, the peptide is FGGFRGRGGFGGFRGRGGFGGFRGRGG (SEQ ID NO. 1), wherein said peptide is capable of inducing disassembly of protein aggregates.

In some embodiments, the peptide is derived from a protein selected from a group comprising Sbp1, Psp2, Gbp2, Scd6, Npl3, Gar1, Ncl1, Nsr1, Nop1/3, Dbp1/2, Ski2, or Lge1.

In some embodiments, protein aggregates are selected from a group comprising TDP43 protein aggregates, FUS protein aggregates, Tau protein aggregates, alpha-synuclein protein aggregates, EWSR1 protein aggregates, TAF15 protein aggregates or combinations thereof.

In some embodiments, protein aggregates are cytoplasmic TDP43 protein aggregates and FUS protein aggregates associated with ALS pathology.

In some embodiments, the peptide is a synthetic peptide comprising an amino acid sequence as set forth as SEQ ID NO. 1, SEQ ID NO. 2, SEQ ID NO. 3, SEQ ID NO. 4, SEQ ID NO. 5, SEQ ID NO. 6, or SEQ ID NO. 7, wherein said peptide is capable of inducing disassembly of TDP43 protein aggregates, FUS protein aggregates, or both.

In some embodiments, the peptide is a synthetic peptide comprising an amino acid sequence as set forth as FGGFRGRGGFGGFRGRGGFGGFRGRGG (SEQ ID NO. 1), wherein said peptide is capable of inducing disassembly of cytoplasmic TDP43 protein aggregates, FUS protein aggregates, or both.

In some embodiments, the peptide is a synthetic peptide comprising an amino acid sequence as set forth as FGGFRGRGGFGGFRGRGGFGGFRGRGG (SEQ ID NO. 1), wherein said peptide is capable of inducing disassembly of cytoplasmic TDP43 protein aggregates, FUS protein aggregates, or both and is derived from Sbp1 protein comprising RGG/RG repetitive motifs.

The present disclosure also provides a composition comprising the peptide of the present disclosure (as described above) and a pharmaceutically acceptable excipient. In some embodiments, the composition is a pharmaceutical composition.

In some embodiments, the pharmaceutically acceptable excipient is a carrier, diluent, stabilizer, buffer, binder, or any combination thereof.

In some embodiments, the composition comprises a peptide comprising an amino acid sequence set forth as $(FGGFRGRGG)_n$ or a sequence having at least 90% sequence identity to said amino acid sequence, wherein 'n' is an integer from 2 to 8, and a pharmaceutically acceptable excipient.

In some embodiments, the composition comprises a peptide having amino acid sequence selected from SEQ ID NOs. 1 to 7 and a pharmaceutically acceptable excipient.

In some embodiments, the carrier is selected from water, saline, lipid-based carriers, or biodegradable polymer.

In some embodiments, the diluent is selected from lactose, mannitol, sorbitol, or dextrose.

In some embodiments, the stabilizer is selected from antioxidants, chelating agents, or preservatives such as EDTA, ascorbic acid, or benzyl alcohol.

In some embodiments, the buffer is selected from phosphate buffer, citrate buffer, or acetate buffer.

In some embodiments, the binder is selected from povidone, microcrystalline cellulose, or hydroxypropyl methylcellulose (HPMC).

Method

The present disclosure also relates to a method to synthesize a disassembly biomolecule that is capable of disassembling protein aggregates. Particularly, the present disclosure provides a method to synthesize a disassembly biomolecule that is capable of disassembling protein aggregates, said method comprising:

c) identifying a disassembly factor in a model system; and d) designing and synthesizing the disassembly biomolecule based on said disassembly factor, wherein the disassembly biomolecule is capable of disassembling protein aggregates.

In some embodiments, the step a) of identifying the disassembly factor in a model system comprises:

i) providing a model system capable of expressing a protein and formation of protein aggregates, under a galactose-inducible promoter;

wherein the model system is a host cell which is a wild-type host cell and a mutant host cell deficient in a candidate disassembly factor;

ii) culturing the wild-type host cell and the mutant host cell in a galactose-containing medium to induce expression of said protein and formation of the protein aggregates;

iii) culturing the wild-type host cell and the mutant host cell in a glucose-containing medium to inhibit expression of said protein and formation of the protein aggregates;

iv) comparing the amount of the protein in the protein aggregates between the wild-type host cell and the mutant host cell; and v) identifying the candidate disassembly factor to be the disassembly factor if the mutant host cell has more protein in the protein aggregates compared to the wild-type host cell.

In some embodiments, the host cell is a yeast cell, and the model system comprises yeast cells for identifying the disassembly factor.

In some embodiments, the yeast cell is selected from *Saccharomyces cerevisiae, Pichia pastoris*, or *Schizosaccharomyces pombe*.

In some embodiments, the yeast cell is *Saccharomyces cerevisiae*.

In some embodiments, the model system comprises *Saccharomyces cerevisiae* cells for identifying the disassembly factor.

In some embodiments, the model system comprises a wild-type yeast cell and a mutant yeast cell, wherein the mutant yeast cell is a deletion mutant strain deficient in a candidate disassembly factor.

In some embodiments, the model system comprises a wild-type yeast cell and a mutant yeast cell, wherein the mutant yeast cell is a deletion mutant strain deficient in a candidate disassembly factor and wherein said wild-type and mutant yeast cells are transformed with one or more plasmids for overexpressing proteins and inducing formation of protein aggregates.

In some embodiments, the model system comprises a wild-type *Saccharomyces cerevisiae* cell and a mutant *Saccharomyces cerevisiae* cell, wherein the mutant *Saccharomyces cerevisiae* cell is deletion mutant strain deficient in a candidate disassembly factor.

In some embodiments, the model system comprises a wild-type *Saccharomyces cerevisiae* cell and a mutant *Saccharomyces cerevisiae* cell, wherein the mutant *Saccharomyces cerevisiae* cell is deletion mutant strain deficient in a candidate disassembly factor and wherein said wild-type and mutant cells are transformed with plasmids for overexpressing proteins and inducing formation of protein aggregates.

In some embodiments, the model system comprises a wild-type *Saccharomyces cerevisiae* cell and a mutant *Saccharomyces cerevisiae* cell, and wherein the mutant *Saccharomyces cerevisiae* cell is deletion mutant strain deficient in Sbp 1 protein (Δsbp1 cells).

In some embodiments, the model system comprises a wild-type *Saccharomyces cerevisiae* cell and a mutant *Saccharomyces cerevisiae* cell, wherein the mutant *Saccharomyces cerevisiae* cell is deletion mutant strain deficient in Sbp 1 protein (Δsbp1 cells) and wherein said wild-type and mutant cells are transformed with the Gal-TDP43-GFP plasmid and for overexpressing TDP43 protein and inducing expression of TDP43 protein aggregates.

In some embodiments, the model system comprises a wild-type *Saccharomyces cerevisiae* cell and a mutant *Saccharomyces cerevisiae* cell, wherein the mutant *Saccharomyces cerevisiae* cell is deletion mutant strain deficient in Sbp 1 protein (Δsbp1 cells) and wherein said wild-type and mutant cells are transformed with the Gal-FUS-YFP plasmid for overexpressing FUS proteins and inducing expression of FUS protein aggregates.

In some embodiments, the host cell expresses protein selected from TDP43 protein, FUS protein, Tau protein aggregates, alpha-synuclein protein aggregates, EWSR1 protein aggregates, TAF15 protein aggregates, or combinations thereof.

In some embodiments, the host cell expresses TDP43 protein and/or FUS protein, and wherein the host cell is yeast cell.

In some embodiments, the host cell expresses TDP43 protein and/or FUS protein, and wherein the host cell is *Saccharomyces cerevisiae* cell.

In some embodiments, the protein aggregates are TDP43 protein aggregates, FUS protein aggregates, Tau protein aggregates, alpha-synuclein protein aggregates, EWSR1 protein aggregates, TAF15 protein aggregates, or combinations thereof.

In some embodiments, the protein aggregates are TDP43 protein aggregates and/or FUS protein aggregates.

In some embodiments, the disassembly factor is a protein containing low-complexity sequences and/or RGG/RG repeat motifs.

In some embodiments, the disassembly factor is a protein or a derivative thereof, selected from a group comprising Sbp1, Psp2, Gbp2, Scd6, Npl3, Gar1, Ncl1, Nsr1, Nop1/3, Dbp1/2, Ski2, and Lge1.

In some embodiments, the disassembly factor is Sbp1 (Single-stranded nucleic acid binding protein) protein containing RGG/RG repeat motifs.

In some embodiments, the step a) of identifying the disassembly factor in a model system comprises:

i) providing a model system capable of expressing TDP43 protein and formation of TDP43 protein aggregates, under a galactose-inducible promoter;

wherein the model system is a yeast host cell which is a wild-type yeast cell and a mutant yeast cell deficient in a candidate disassembly factor;

ii) culturing the wild-type yeast cell and the mutant yeast cell in a galactose-containing medium to induce expression of TDP43 protein and formation of the TDP43 protein aggregates;

iii) culturing the wild-type yeast cell and the mutant yeast host cell in a glucose-containing medium to inhibit expression of said TDP43 protein and formation of the TDP43 protein aggregates;

iv) comparing the amount of the TDP43 protein in the TDP43 protein aggregates between the wild-type yeast cell and the mutant yeast cell; and v) identifying the candidate disassembly factor to be the disassembly factor if the mutant yeast cell has more TDP43 protein in the TDP43 protein aggregates compared to the wild-type yeast cell, wherein the candidate disassembly factor is Sbp1 protein.

In some embodiments, the step a) of identifying the disassembly factor in a model system comprises:

i) providing a model system capable of expressing FUS protein and formation of FUS protein aggregates, under a galactose-inducible promoter;

wherein the model system is a yeast host cell which is a wild-type yeast cell and a mutant yeast cell deficient in a candidate disassembly factor;

ii) culturing the wild-type yeast cell and the mutant yeast cell in a galactose-containing medium to induce expression of FUS protein and formation of the FUS protein aggregates;

iii) culturing the wild-type yeast cell and the mutant yeast cell in a glucose-containing medium to inhibit expression of said FUS protein and formation of the FUS protein aggregates;

iv) comparing the amount of the FUS protein in the FUS protein aggregates between the wild-type yeast cell and the mutant yeast cell; and v) identifying the candidate disassembly factor to be the disassembly factor if the mutant yeast cell has more FUS protein in the FUS protein aggregates compared to the wild-type yeast cell, wherein the candidate disassembly factor is Sbp1 protein.

In some embodiments, the step a) of identifying the disassembly factor in a model system comprises:

i) providing a model system capable of expressing TDP43 protein and formation of TDP43 protein aggregates, under a galactose-inducible promoter;

wherein the model system is a *Saccharomyces cerevisiae* host cell which is a wild-type *Saccharomyces cerevisiae* cell and a mutant *Saccharomyces cerevisiae* cell deficient in a candidate disassembly factor;

ii) culturing the wild-type *Saccharomyces cerevisiae* cell and the mutant yeast *Saccharomyces cerevisiae* cell in a galactose-containing medium to induce expression of TDP43 protein and formation of the TDP43 protein aggregates;

iii) culturing the wild-type *Saccharomyces cerevisiae* cell and the mutant *Saccharomyces cerevisiae* cell in a glucose-containing medium to inhibit expression of said TDP43 protein and formation of the TDP43 protein aggregates;

iv) comparing the amount of the TDP43 protein in the TDP43 protein aggregates between the wild-type *Saccharomyces cerevisiae* cell and the mutant *Saccharomyces cerevisiae* cell; and v) identifying the candidate disassembly factor to be the disassembly factor if the mutant *Saccharomyces cerevisiae* cell has more TDP43 protein in the TDP43 protein aggregates compared to the wild-type *Saccharomyces cerevisiae* cell, wherein the candidate disassembly factor is Sbp1 protein.

In some embodiments, the step a) of identifying the disassembly factor in a model system comprises:

i) providing a model system capable of expressing FUS protein and formation of FUS protein aggregates, under a galactose-inducible promoter;

wherein the model system is a *Saccharomyces cerevisiae* host cell which is a wild-type *Saccharomyces cerevisiae* cell and a mutant *Saccharomyces cerevisiae* cell deficient in a candidate disassembly factor;

ii) culturing the wild-type *Saccharomyces cerevisiae* cell and the mutant yeast *Saccharomyces cerevisiae* cell in a galactose-containing medium to induce expression of FUS protein and formation of the FUS protein aggregates;

iii) culturing the wild-type *Saccharomyces cerevisiae* cell and the mutant *Saccharomyces cerevisiae* cell in a glucose-containing medium to inhibit expression of said FUS protein and formation of the FUS protein aggregates;

iv) comparing the amount of the FUS protein in the FUS protein aggregates between the wild-type *Saccharomyces cerevisiae* cell and the mutant *Saccharomyces cerevisiae* cell; and v) identifying the candidate disassembly factor to be the disassembly factor if the mutant *Saccharomyces cerevisiae* cell has more FUS protein in the FUS protein aggregates compared to the wild-type *Saccharomyces cerevisiae* cell, wherein the candidate disassembly factor is Sbp1 protein.

In some embodiments, designing a disassembly biomolecule based on the identified disassembly factor in step a) comprises comparing sequence of a motif of the disassembly factor with a homologous motif from another protein to identify a repetitive amino acid motif responsible for disassembly activity.

In some embodiments, designing a disassembly biomolecule based on the identified disassembly factor in step a) comprises comparing sequence of a RGG motif of the Sbp1 protein with a homologous RGG motif from another protein, i.e., Nucleolin, to identify a repetitive amino acid RGG/RG motif responsible for or capable of inducing disassembly of protein toxic aggregates, wherein said protein toxic aggregates are associated with neurodegenerative diseases.

In some embodiments, the disassembly biomolecule is the peptide of the present disclosure, i.e., peptide comprising an amino acid sequence set forth as $(FGGFRGRGG)_n$ or a sequence having at least 90% sequence identity to said amino acid sequence, wherein 'n' is an integer from 2 to 8, and wherein said peptide is capable of disassembling protein aggregates.

In certain embodiments, the disassembly biomolecule comprises a peptide having an amino acid sequence as set forth in any one of SEQ ID NOs: 1 to 7 and is capable of disassembling TDP43 and/or FUS protein aggregates.

In some embodiments, the disassembly biomolecule is a peptide comprising an amino acid sequence as set forth as FGGFRGRGGFGGFRGRGGFGGFRGRGG (SEQ ID NO.

1), wherein said peptide is capable of inducing disassembly of TDP43 protein aggregates, FUS protein aggregates, or both and is derived from Sbp1 protein comprising RGG/RG repetitive motifs.

While the subsequent embodiments focus on methods, the features and characteristics of the peptide are as described by any of the embodiments above. For the sake of brevity, and avoiding repetition, each of those embodiments are not being reiterated here again. However, each of the said embodiments completely fall within the purview of methods, described herein.

In some embodiments, the disassembly biomolecule is synthesized by expressing a nucleotide sequence encoding said disassembly biomolecule in a prokaryotic or a eukaryotic expression system and purifying the resulting disassembly biomolecule, wherein the disassembly biomolecule is the peptide comprising an amino acid sequence set forth as $(FGGFRGRGG)_n$ or a sequence having at least 90% sequence identity to said amino acid sequence, wherein 'n' is an integer from 2 to 8.

In some embodiments, the disassembly biomolecule is synthesized by expressing a nucleotide sequence encoding said disassembly biomolecule in a prokaryotic or a eukaryotic expression system and purifying the resulting disassembly biomolecule, wherein the disassembly biomolecule is the peptide comprising an amino acid sequence of SEQ ID NO. 1.

In some embodiments, the prokaryotic expression system comprises a bacterial cell; and the eukaryotic expression system comprises a eukaryotic cell.

In some embodiments, the bacterial cell is selected from *E. coli, Bacillus subtilis, Pseudomonas* spp., *Streptomyces* spp.

In some embodiments, the eukaryotic cell is selected from *Saccharomyces cerevisiae, Pichia pastoris*, insect cells or cell lines.

In some embodiments, the peptide encoding DNA sequence is devised and cloned into a bacterial expression vector with His-tag at the N-terminal for purification. The peptide is then induced into *E. coli* and purified using Ni-NTA resin.

In some embodiments, the disassembly biomolecule is synthesized by chemical synthesis, i.e., solid-phase peptide synthesis (SPPS), wherein the disassembly biomolecule is the peptide comprising an amino acid sequence set forth as $(FGGFRGRGG)_n$ or a sequence having at least 90% sequence identity to said amino acid sequence, wherein 'n' is an integer from 2 to 8.

In some embodiments, the disassembly biomolecule is synthesized by chemical synthesis, i.e., solid-phase peptide synthesis (SPPS), wherein the disassembly biomolecule is the peptide comprising an amino acid sequence of SEQ ID NO. 1.

In some embodiments, the method further comprises a step of assessing the ability of the disassembly biomolecule to disassemble the protein aggregates in an in vitro assay or an in-cell sedimentation assay.

In some embodiments, the in-cell sedimentation assays is performed by enriching protein aggregates from mammalian cells.

In some embodiments, the mammalian cells are selected from HEK293T cells, HeLa cells, N2A cells, SHSY5Y cells, U2OS cells, iPSCs, NSC34 cells, mouse embryonic fibroblasts.

In some embodiments, the host cell expressing Sbp1 protein significantly reduces levels of FUS-P525L condensates by shifting the protein to the soluble fraction. In some embodiments, the host cell expressing mutant version of Sbp1 lacking the RGG motif (Sbp1ΔRGG) does not show disassembly.

In some embodiments, the method to synthesize the disassembly biomolecule that is capable of disassembling protein aggregates, comprises:

a) identifying a disassembly factor in a yeast model system;

b) designing and synthesizing the disassembly biomolecule based on said disassembly factor, wherein the disassembly biomolecule is capable of disassembling protein aggregates; and c) assessing the ability of the disassembly biomolecule to disassemble the protein aggregates.

In some embodiments, the method to synthesize the disassembly biomolecule that is capable of disassembling protein aggregates, comprises:

a) identifying a disassembly factor in a yeast model system;

b) designing and synthesizing the disassembly biomolecule based on said disassembly factor in a bacterial system; and c) assessing the ability of the disassembly biomolecule to disassemble the protein aggregates in an in vitro assay or an in-cell sedimentation assay in a mammalian system, wherein the disassembly factor is Sbp1 protein; and wherein the disassembly biomolecule is a peptide comprising amino acid sequence of SEQ ID NO. 1.

In some embodiments, the method to synthesize the disassembly biomolecule that is capable of disassembling protein aggregates, comprises:

a) identifying a disassembly factor in a yeast model system;

i. providing a model system capable of expressing TDP43 protein and formation of TDP43 protein aggregates, under a galactose-inducible promoter;
      wherein the model system is a yeast host cell which is a wild-type yeast cell and a mutant yeast cell deficient in a candidate disassembly factor;

ii. culturing the wild-type yeast cell and the mutant yeast cell in a galactose-containing medium to induce expression of TDP43 protein and formation of the TDP43 protein aggregates;

iii. culturing the wild-type yeast cell and the mutant yeast host cell in a glucose-containing medium to inhibit expression of said TDP43 protein and formation of the TDP43 protein aggregates;

iv. comparing the amount of the TDP43 protein in the TDP43 protein aggregates between the wild-type yeast cell and the mutant yeast cell; and v. identifying the candidate disassembly factor to be the disassembly factor if the mutant yeast cell has more TDP43 protein in the TDP43 protein aggregates compared to the wild-type yeast cell, wherein the candidate disassembly factor is Sbp1 protein;

b) designing and synthesizing the disassembly biomolecule based on said disassembly factor, wherein designing the disassembly biomolecule based on the identified disassembly factor in step a) comprises comparing sequence of a motif of the disassembly factor with a homologous motif from another protein to identify a repetitive amino acid motif responsible for disassembly activity, and wherein the disassembly biomolecule is synthesized by chemical synthesis, i.e., solid-phase peptide synthesis (SPPS); and c) assessing the ability of the disassembly biomolecule to disassemble the protein aggregates in an in vitro assay or an in-cell sedimentation assay, wherein the disassembly factor is Sbp1 protein; and wherein the disassembly biomolecule is a peptide comprising amino acid sequence of SEQ ID NO. 1.

The present disclosure also provides a method to disassemble protein aggregates. More particularly, the present disclosure provides a method to disassemble protein aggregates comprising contacting the peptide (as described above), or the composition (as described above), with target cell(s) comprising said protein aggregates, to disassemble the protein aggregates.

While the subsequent embodiments focus on methods, the features and characteristics of the peptide and composition are as described by any of the embodiments above. For the sake of brevity, and avoiding repetition, each of those embodiments are not being reiterated here again.

However, each of the said embodiments completely fall within the purview of methods, described herein.

In some embodiments, the target cells are selected from a group comprising mammalian cells, neuroblastoma cells, motor neurons, cortical neurons, astrocytes, oligodendrocytes, primary neuronal cultures, microglia, induced pluripotent stem cells (iPSCs), HEK293 cells, HeLa cells, or other relevant cell lines.

In some embodiments, the target cells are in present in a subject.

In some embodiments, the subject is a human individual suffering from a neurodegenerative disease selected from amyotrophic lateral sclerosis (ALS), frontotemporal dementia (FTD), Alzheimer's disease, or Parkinson's disease.

In some embodiments, the method to disassemble protein aggregates is an in vitro method that is performed under controlled laboratory conditions, intended for both clinical investigations and research applications.

The present disclosure also provides a method of treating a disorder associated with protein aggregates in a subject in need thereof, the method comprising administering to the subject a therapeutically effective amount of a peptide having amino acid selected from SEQ ID NOs. 1 to 7, or a pharmaceutical composition comprising said peptide.

In some embodiments, the subject is a human individual.

In some embodiments, the disorder associated with protein aggregates is selected from amyotrophic lateral sclerosis (ALS), frontotemporal dementia (FTD), Alzheimer's disease, or Parkinson's disease.

In some embodiments, the method refers to a method of treating ALS in a subject in need thereof, the method comprising administering to the subject a therapeutically effective amount of a peptide having amino acid sequence SEQ ID NO. 1, or a composition comprising said peptide.

Use

The present disclosure also provides the use of the peptide (as described above) and the composition (as described above).

More particularly, the present disclosure provides a peptide comprising an amino acid sequence set forth as $(FGGFRGRGG)_n$ or a sequence having at least 90% sequence identity to said amino acid sequence, wherein 'n' is an integer from 2 to 8, or a composition comprising said peptide for use as a medicament.

In some embodiments, the present disclosure provides a peptide comprising an amino acid sequence set forth as $(FGGFRGRGG)_n$ or a sequence having at least 90% sequence identity to said amino acid sequence, wherein 'n' is an integer from 2 to 8, or a composition comprising said peptide, for use as a medicament for disassembling protein aggregates.

In some embodiments, the present disclosure provides a peptide comprising an amino acid sequence set forth as $(FGGFRGRGG)_n$ or a sequence having at least 90% sequence identity to said amino acid sequence, wherein 'n' is an integer from 2 to 8, or a composition comprising said peptide, for use in a method of treatment of a neurodegenerative disease characterized by protein aggregates.

In some embodiments, the present disclosure provides a peptide having sequence selected from SEQ ID NO. 1 to 7 for use as a medicament. The present disclosure provides a composition comprising a peptide having a sequence selected from SEQ ID NO: 1 to 7 for use as a medicament.

In some embodiments, the present disclosure provides the peptide having sequence selected from SEQ ID NO. 1 to 7, or a composition comprising a peptide having a sequence selected from SEQ ID NO: 1 to 7 for use as a medicament for disassembling protein aggregates.

In some embodiments, the present disclosure provides the peptide having sequence selected from SEQ ID NO. 1 to 7, or a composition comprising a peptide having a sequence selected from SEQ ID NO: 1 to 7 for use in a method of treatment of a neurodegenerative disease characterized by protein aggregates.

In some embodiments, the present disclosure provides a peptide having an amino acid sequence selected from SEQ ID NOs: 1 to 7, or a composition comprising a peptide having a sequence selected from SEQ ID NO: 1 to 7 for use in the treatment of neurodegenerative disorders selected from amyotrophic lateral sclerosis (ALS), frontotemporal dementia (FTD), Alzheimer's disease, or Parkinson's disease.

In some embodiments, the use of a peptide comprising an amino acid sequence set forth as $(FGGFRGRGG)_n$ or a sequence having at least 90% sequence identity to said amino acid sequence, wherein 'n' is an integer from 2 to 8, or a composition comprising said peptide, for the manufacture of a medicament for the treatment of a disease characterized by protein aggregates.

In some embodiments, the use of a peptide having an amino acid sequence selected from SEQ ID NOs: 1 to 7 or a composition comprising a peptide having an amino acid sequence selected from SEQ ID NOs: 1 to 7, for the manufacture of a medicament for the treatment of a disease characterized by protein aggregates.

In some embodiments, the use of a peptide having an amino acid sequence selected from SEQ ID NOs: 1 to 7 or a composition comprising a peptide having a sequence selected from SEQ ID NO: 1 to 7 for the manufacture of a medicament for the treatment of neurodegenerative disorders selected from ALS, frontotemporal dementia (FTD), or Alzheimer's disease, Parkinson's disease.

Thus, the present disclosure provides a novel disassembly biomolecule, specifically a peptide based on a repetitive motif or a low complexity sequence. The said peptide is potent and effective in disassembly of protein aggregates associated with neurological diseases and has potential for therapeutic applications. The present disclosure also provides a robust method or a platform technology for synthesizing and/or identifying disassembly biomolecules that are capable of inducing disassembly of protein aggregates associated with neurodegenerative diseases. The unique aspects or features of the present disclosure are as follows:

The novelty/uniqueness resides in utilizing yeast cells as a model system for identifying disassembly factors.

Although yeast has been used to investigate the toxicity associated with TDP43 and FUS, there are no prior known reports describing its use for identifying or characterizing disassembly factors.

Another distinctive feature of the present disclosure is the identification of phenylalanine (F)-, arginine (R)-, and glycine (G)-rich peptides through the described platform technology. These peptides belong to the class of low-complexity sequences, which have predominantly been associated with the assembly of biomolecular condensates, rather than their disassembly. Furthermore, R- and G-rich sequences have previously been implicated in promoting disease phenotypes through aggregation. In contrast, the present disclosure defies the teachings of the prior art by demonstrating a novel and counterintuitive role of these peptides in the disassembly of TDP43 and FUS condensates.

Advantages of Present Disclosure

The present disclosure exhibits at least the following advantages:

The application of peptides as a therapeutic modality offers significant advantages. Their small size facilitates better tissue penetration and bioavailability, and their intrinsic positive charge enhances cellular uptake, potentially eliminating the need for additional cell-penetrating sequences. These features make the peptides highly suitable for intracellular targeting of toxic protein aggregates.

The present invention also provides a robust platform technology for identifying peptides capable of disassembling toxic protein aggregates. This platform involves a three-step screening and validation process conducted across multiple biological systems:

- Initial screening and identification of candidate peptides in yeast model;
- Expression and purification (or chemical synthesis) of the selected peptides in prokaryotic cell; and
- Functional validation using mammalian cell-derived RNP condensates.
- This modular and adaptable approach can be readily extended to other disease-relevant proteins such as C9ORF72 (ALS), α-synuclein (Parkinson's disease), and huntingtin (Huntington's disease), all of which are associated with pathological protein aggregation. Given the conserved mechanistic basis of protein aggregates across multiple neurodegenerative conditions, this invention provides a versatile platform with broad therapeutic potential.

It is to be understood that the foregoing description is illustrative and not limiting. While considerable emphasis has been placed herein on particular features of this disclosure, it will be appreciated that various modifications can be made, and that many changes can be made in the preferred embodiments without departing from the principles of the disclosure. Those skilled in the art will recognize that the embodiments herein can be practiced with modification within the spirit and scope of the embodiments as described herein. Similarly, additional embodiments and features of the present disclosure will be apparent to one of ordinary skill in art based upon description provided herein.

Descriptions of well-known/conventional methods/steps and techniques are omitted so as to not unnecessarily obscure the embodiments herein. Further, the disclosure herein provides for examples illustrating the above-described embodiments, and in order to illustrate the embodiments of the present disclosure, certain aspects have been employed. The examples used herein for such illustration are intended merely to facilitate an understanding of ways in which the embodiments may be practiced and to further enable those of skill in the art to practice the embodiments. Accordingly, following examples should not be construed as limiting the scope of the embodiments herein.

EXAMPLES

Example 1: Employing Yeast Based Model System to Identify a Disassembly Factor Heterologous expression of ALS-associated proteins TDP43 and FUS in *Saccharomyces cerevisiae* has been shown to induce their aggregation, resulting in the formation of ribonucleoprotein (RNP) condensates and exerting cytotoxic effects on yeast cells. Given the pathological relevance of such condensates, the present study utilized yeast as a model system to investigate the disassembly mechanisms of TDP43 and FUS aggregates. It was observed that deletion of specific disassembly factors in yeast leads to the accumulation of TDP43/FUS condensates, indicating impaired disassembly. To identify such genetic determinants, various deletion strains were analysed for their disassembly phenotypes by repressing galactose-induced expression of TDP43/FUS through growth in glucose-containing media (FIG. 1).

The overexpression of ALS-associated proteins, TDP43 and FUS, is toxic to yeast cells, and multiple reports have identified the modulators of this phenotype. Overexpression can be carried out by expressing the target protein under a galactose-inducible promoter, as has been done for both TDP43 and FUS. By using the present model system, the inventors understood the role of RGG-motif-containing protein Sbp1 in the disassembly of TDP43 and FUS condensates.

Experiment:

In the present example, *Saccharomyces cerevisiae* cells overexpressing TDP43 and FUS under a galactose-inducible promoter were incubated in galactose-containing media to induce the expression of TDP43/FUS. During this phase, the induced TDP43/FUS protein causes stress (termed 'induction') and accumulates in the cytoplasmic condensates (FIGS. 2A and D). FIG. 2 (A) shows the representative images for the microscopy analysis of wild-type and Δsbp1 cells transformed with the Gal-TDP43-GFP plasmid. After growing to 0.4 $OD_{600}$, cells were shifted to galactose-containing media for 3 hours to induce TDP43 expression (stress induction), followed by 4 hours of recovery in glucose (stress recovery). Cells were taken for microscopy analysis at both steps. White arrows in FIG. 2(A) mark the presence of TDP43 condensates. FIG. 2 (B) is a graph representing the fraction of the TDP43 protein present in condensates per cell. Condensate intensities were calculated and divided by the total fluorescent intensity of the respective cell. A minimum of 50 cells per experiment were analyzed from 4 independent experiments (n=4) as performed in A. An unpaired t-test was used to calculate the significance. FIG. 2 (C) is a graph depicting the relative change in TDP43 protein levels as compared to the respective induction condition. Significance was calculated using a student-paired t-test analysis (n=8).

FIG. 2 (D) are the representative images for the microscopy analysis of wild-type and Δsbp1 cells transformed with Gal-FUS-YFP plasmid. After growing to 0.4 $OD_{600}$, cells were shifted to galactose-containing media for 2 hours to induce FUS expression (stress induction), followed by 4 hours of recovery in glucose (stress recovery). Cells were taken for microscopy analysis at both steps. White arrows in FIG. 2 (D) mark the presence of FUS condensates. FIG. 2 (E) illustrates a graph representing the fraction of the FUS protein in condensates per cell. Condensate intensities were calculated and divided by the total fluorescent intensity of the respective cell. A minimum of 50 cells per experiment were analyzed from 5 independent experiments as performed in D (n=5). An unpaired t-test was used to calculate the significance. FIG. 2 (F) shows a graph depicting the relative change in FUS protein levels compared to the respective induction condition. Significance was calculated using a student-paired t-test analysis (n=5).

After induction, the cells were allowed to grow in glucose-containing media. During this growth time, the protein levels reduced because of the inhibition of the galactose promoter in glucose media. This reduction led to the rescue of cells from stress (termed 'recovery') and a subsequent decrease in the number of condensates. The amount of protein present in the condensates was then assessed and compared between wild-type and Δsbp1 cells to understand the role of Sbp1 protein in the assembly and disassembly of the TDP43/FUS condensates.

Results:

The induction of TDP43 condensates was first assessed in wild-type and Δsbp1 cells. The fraction of protein present in the condensates was comparable in both backgrounds after induction (FIGS. 2A and 2B). However, the fraction of TDP43 protein in condensates during recovery was observed to be higher in the Δsbp1 background than in the wild-type cells (FIGS. 2A and 2B). The dynamics of FUS condensates also followed a similar trend in the Δsbp1 as compared to the wild-type background (FIGS. 2D and 2E). While the fraction of FUS protein localized to condensates was comparable between wild type and Δsbp1, there was a significant defect in the disassembly of protein out of condensates during recovery from stress induced by FUS overexpression (FIGS. 2D and 2E). These observations highlight the importance of Sbp1 in regulating the disassembly of TDP43 and FUS condensates in yeast cells.

One of the possible reasons for the disassembly defect in the Δsbp1 background could be because of an increase in TDP43 and FUS levels. To understand this, the total protein levels for TDP43 and FUS were compared by Western analysis (FIGS. 2C and 2F). The relative levels of protein reduction were comparable in different backgrounds for both TDP43 and FUS. Therefore, the defective disassembly could not be attributed to TDP43 and FUS protein accumulation in the Δsbp1 background.

The above experimental results demonstrate that Sbp1 protein has a role to play in the disassembly of TDP43 and FUS condensates in yeast cells.

Example 2: Designing and Synthesis of Disassembly Biomolecule

Based on the protein identified that has the disassembly phenotype, the sequence motif necessary for the specific function can be elucidated experimentally by using deletion constructs. For this, in-vitro and in-cell sedimentation assays were utilized (FIG. 3). Such information was further extended to compare the sequence architecture of similar motifs originating from different proteins. Comparisons were made between the paralogs from the same or homologs from other organisms. Using such a comparison, a repetitive motif or a set of specific amino acids can be identified as a putative disassembly peptide.

For purification, the peptide encoding DNA sequence was devised and cloned into a bacterial expression vector with His-tag at the N-terminal for purification. The peptide can be induced in *E. coli* and purified using Ni-NTA resin. Alternatively, the peptide can also be chemically synthesized from any peptide synthesizing companies.

Experiment:

The disassembly activity of Sbp1 and its RGG-motif deletion mutant was assessed on enriched FUS-P525L (a mutant form of FUS identified in many ALS cases) condensates from HEK293T cells by using a modified in-cell sedimentation assay. Briefly, a recombinant Sbp1 was incubated with the enriched condensates of FUS-P525L and incubated for 1 hour at 30° C. (FIG. 4A). The supernatant (soluble) and pellet (insoluble) fractions were then separated by centrifugation at 18000 g for 15 minutes. If Sbp1 affects the disassembly of FUS mutant condensates, FUS protein will partition more in the supernatant (soluble) phase upon incubation with purified Sbp1 compared to the control (buffer) condition. Western analysis was carried out to check protein distribution in soluble and insoluble fractions. GAPDH, a soluble cytoplasmic protein, did not partition into the pellet fraction as expected (FIG. 4A). On the contrary, FUS-P525L localization to the cytoplasmic condensates would lead to its enrichment to the insoluble pellet fraction (FIG. 4A). Strikingly, the incubation with Sbp1 resulted in a significant redistribution of FUS-P525L protein to the soluble phase (FIGS. 4A and 4B). Such a phenotype was not observed for buffer control. Interestingly, when the RGG-motif deletion mutant of Sbp1 was assessed for its disassembly activity on the FUS-P525L mutant, a significant defect was observed as compared to the full-length protein (FIGS. 4A and 4B). These observations suggest the RGG-dependent disassembly activity of Sbp1 on the enriched FUS-P525L condensates.

A simple two-component purified system-based sedimentation assay was also performed to address whether Sbp1 could directly affect mutant FUS condensates (in-vitro sedimentation assay). Purified recombinant FUS or TDP43 protein was subjected to phase separation to form the condensates in-vitro (FIG. 4C). Purified Sbp1 or Sbp1ΔRGG protein was then incubated with these pre-formed condensates to assess their impact. Interestingly, upon incubation with Sbp1, there was a significant enrichment of FUS in the supernatant fraction (FIGS. 4D and 4E). Further, the fraction of FUS protein in the supernatant increased with increasing concentration of Sbp1. Such a phenotype was not observed for the control reaction, where an equal amount of BSA was incubated with the pre-formed condensates. Moreover, as observed for the in-cell sedimentation assay, the extent of partitioning was also significantly defective after incubation with the Sbp1ΔRGG protein (FIGS. 4D and 4E). Therefore, with these observations from in-cell and in-vitro sedimentation assays, the necessity of the RGG-motif of Sbp1 was identified for the disassembly of FUS condensates. Based on these results, the Sbp1-RGG motif was compared with that of a similar RGG motif-containing protein from mammalian cells, Nucleolin. The sequence comparison identified the amino acid phenylalanine (F) as one of the unique peptide features between the RGG/RG repeats of both proteins. Therefore, the inventors synthesized a peptide with such a property that the phenylalanine residue flanks every RGG/RG motif. The peptide thus designed (named FRG) consisted of the repetitive motif: $(FGGFRGRGG)_3$. Notably, such a peptide sequence does not exist in nature alone.

Thus, in conclusion, the above experimental data establishes a platform/methodology for identifying peptides capable of disassembling toxic protein aggregates. Using in-cell and in-vitro assays, the disassembly activity of Sbp1 was shown to depend on its RGG motif, particularly phenylalanine (F)-flanked RGG/RG repeats. Comparative analysis with Nucleolin guided the design of a novel synthetic peptide, FRG, with the motif $(FGGFRGRGG)_3$. This peptide, not found in nature, represents a unique and rationally designed disassembly agent with potential for treating neurodegenerative diseases associated with protein aggregation.

Example 3: Testing the Synthesized Peptide for their Ability to Disassemble Protein Aggregates In-cell sedimentation assay was used to check the potential activity of the peptide (FRG peptide synthesized in example 2) as a disassembly factor. For this assay, the chemically synthesized peptide was added to the phase-separated FUS structures derived from cells (in-cell sedimentation). The positive target should disassemble these structures, which will lead to the accumulation of proteins in the soluble phase (FIG. 3).

Experiment:

The disassembly activity of the FRG peptide was assessed by the in-cell sedimentation assay (as described in FIG. 3). The addition of the FRG peptide significantly induced the redistribution of FUS-P525L protein to the soluble phase as compared to the buffer control, thus identifying a novel disassembly factor (FIGS. 5A and 5B). The FRG peptide significantly increased the soluble fraction of FUS-P525L protein (33% increase), compared to the buffer control. Thus, it was found that the FRG peptide leads to the disassembly of FUS condensates.

The above experimental data/results demonstrate the effectiveness of the yeast model in investigating the disassembly mechanisms of TDP43 and FUS protein aggregates, the key contributors to ALS pathology and identifying novel peptides which are capable of inducing disassembly of protein aggregates. Particularly, the experimental data identified Sbp1 as a crucial factor in driving disassembly, with its RGG motif playing an essential role. This was supported by both in-cell and in-vitro sedimentation assays, which showed that Sbp1 could significantly reduce levels of FUS-P525L condensates by shifting the protein to the soluble fraction. In contrast, a mutant version of Sbp1 lacking the RGG motif (Sbp1ΔRGG) failed to show disassembly, emphasizing the importance of this sequence element/amino acid motif. Building on these observations, the present inventors successfully designed a synthetic peptide, FRG $(FGGFRGRGG)_3$, which showed strong disassembly activity against FUS condensates in cell-based assays, making it a promising candidate for therapeutic development. Together, these results offer a potential path toward targeted strategies for addressing ALS and other neurodegenerative diseases linked to protein aggregation.

The inventors have also devised the possible mechanism of action of the claimed peptide. There are following two possibilities of the peptide interaction with the protein condensates:

1. The protein complexes of FUS and TDP43 have many protein-protein interaction networks necessary to maintain their integrity. The peptide of the present disclosure might directly interact with the LCS (low complexity sequences) of TDP43 and FUS and outcompetes these essential interactions. Such an activity will bring condensate-residing proteins out of the RNP condensate, thus orchestrating the disassembly phenotype.
2. Because of the higher positive charge, the peptide of the present disclosure can interact with a type of nucleic acid, RNA. Apart from proteins, many RNAs are also crucial for the integrity of disease-associated condensates. The peptide of the present disclosure might interact with such RNAs more strongly than the other condensate-residing proteins. This will lead to competition-mediated disassembly of these structures.

The experimental findings exemplify the successful application of the claimed method in identifying and validating a novel synthetic peptide, FRG, with potent disassembly activity against pathological protein aggregates. This data highlights the broader utility of the yeast model system and the integrated approach, which includes screening in yeast, purification via a bacterial expression system, and validation in mammalian cells, as an effective platform for discovering disassembly biomolecules. While the results specifically demonstrate activity against TDP43 and FUS aggregates associated with ALS, the method is equally adaptable for targeting aggregates linked to other neurodegenerative diseases, including those involving C9ORF72, α-synuclein, or huntingtin. Importantly, although the FRG peptide is exemplified herein, the strategy enables rational design of additional similar peptides incorporating similar or extended motifs, which are expected to exhibit comparable disassembly potential. Thus, the invention provides a robust framework for developing therapeutic agents targeting a broad spectrum of protein aggregates-related disorders.

The foregoing description of the specific embodiments reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments in this disclosure have been described in terms of preferred embodiments, those skilled in the art will recognize that the embodiments herein can be practiced with modification within the spirit and scope of the embodiments as described herein.

Throughout this specification, the term 'combinations thereof' or 'any combination thereof' or 'any combinations thereof' are used interchangeably and are intended to have the same meaning, as regularly known in the field of patents disclosures.

As regards the embodiments characterized in this specification, it is intended that each embodiment be read independently as well as in combination with another embodiment. For example, in case of an embodiment 1 reciting 3 alternatives A, B and C, an embodiment 2 reciting 3 alternatives D, E and F and an embodiment 3 reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Any discussion of documents, acts, materials, devices, articles, and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

We claim:

1. A peptide comprising an amino acid sequence of $(FGGFRGRGG)_n$ or a sequence having at least 90% sequence identity thereto, wherein 'n' is an integer from 2 to 8, and wherein said peptide is capable of disassembling protein aggregates associated with neurodegenerative diseases.

2. The peptide as claimed in claim 1, wherein the protein aggregates are selected from a group comprising TDP43 protein aggregates, FUS protein aggregates, Tau protein aggregates, alpha-synuclein protein aggregates, EWSR1 protein aggregates, TAF15 protein aggregates or combinations thereof.

3. The peptide as claimed in claim 1, wherein the peptide is (SEQ ID NO. 1)
FGGFRGRGGFGGFRGRGGFGGFRGRGG, (SEQ ID NO. 2)
FGGFRGRGGFGGFRGRGG, -continued (SEQ ID NO. 3)
FGGFRGRGGFGGFRGRGGFGGFRGRGGFGGFRGRGG, (SEQ ID NO. 4)
FGGFRGRGGFGGFRGRGGFGGFRGRGGFGGFRGRGGFGGFRGRGG, (SEQ ID NO. 5)
FGGFRGRGGFGGFRGRGGFGGFRGRGGFGGFRGRGGFGGFRGRGGFGGF
RGRGG, (SEQ ID NO. 6)
FGGFRGRGGFGGFRGRGGFGGFRGRGGFGGFRGRGGFGGFRGRGGFGGF
RGRGGFGGFRGRGG,
or (SEQ ID NO. 7)
FGGFRGRGGFGGFRGRGGFGGFRGRGGFGGFRGRGGFGGFRGRGGFGGF
RGRGGFGGFRGRGGFGGFRGRGG.

4. The peptide as claimed in claim 1, wherein said peptide is a disassembly biomolecule that is capable of inducing disassembly of TDP43 protein aggregates or FUS protein aggregates or both.

* * * * *